United States Patent
Carroll

(10) Patent No.: US 10,023,584 B2
(45) Date of Patent: Jul. 17, 2018

(54) TETRANDRINE FAMILY PHARMACEUTICAL FORMULATIONS AND METHOD

(71) Applicant: CBA Pharma, Inc., Lexington, KY (US)

(72) Inventor: Ron D. Carroll, Fayetteville, NY (US)

(73) Assignee: CBA Pharma, Inc., Lexington, KY (US)

(*) Notice: Subject to any disclaimer, the term of this patent is extended or adjusted under 35 U.S.C. 154(b) by 0 days.

(21) Appl. No.: 15/346,022

(22) Filed: Nov. 8, 2016

(65) Prior Publication Data

US 2017/0050975 A1    Feb. 23, 2017

Related U.S. Application Data

(62) Division of application No. 14/199,235, filed on Mar. 6, 2014, now Pat. No. 9,517,234.

(60) Provisional application No. 61/792,849, filed on Mar. 15, 2013.

(51) Int. Cl.
| | |
|---|---|
| *A61K 31/4748* | (2006.01) |
| *C07D 491/147* | (2006.01) |
| *A61K 45/06* | (2006.01) |
| *A61K 31/4741* | (2006.01) |
| *A61K 9/48* | (2006.01) |

(52) U.S. Cl.
CPC ........... *C07D 491/147* (2013.01); *A61K 9/48* (2013.01); *A61K 9/485* (2013.01); *A61K 9/4858* (2013.01); *A61K 9/4866* (2013.01); *A61K 31/4741* (2013.01); *A61K 45/06* (2013.01)

(58) Field of Classification Search
USPC ............................................ 514/279; 546/35
See application file for complete search history.

(56) References Cited

U.S. PATENT DOCUMENTS

| | | | |
|---|---|---|---|
| 5,627,195 A | 5/1997 | Hu | |
| 6,218,541 B1 | 4/2001 | Wang | |

FOREIGN PATENT DOCUMENTS

| | | |
|---|---|---|
| CN | 1187123 A | 7/1998 |
| CN | 102898433 A | 1/2013 |
| EP | 2420496 A2 | 12/2014 |
| EP | 2902028 | 8/2015 |
| JP | 62207216 | 9/1987 |
| JP | 62209018 | 9/1987 |
| JP | 63179878 | 7/1988 |
| JP | 2243627 | 9/1990 |
| JP | 499723 | 3/1992 |
| JP | 2003523954 | 8/2003 |
| JP | 2009545581 | 8/2003 |
| JP | 2011512416 | 4/2011 |
| WO | 2014043336 | 3/2014 |

OTHER PUBLICATIONS

Yi-Chao Hsu, et al., "Antifribrotic effects of tetrandrine on hepatic stellate cells and rats with liver fibrosis," Journal of Gastroenterology and Hepatology, vol. 22, No. 1, Jan. 1, 2007 (Jan. 1, 2007), pp. 99-111.

Cai Yan, et al., "Tetrandrine-induced apoptosis in rat primary hepatocytes is initiated from mitochondria: Caspases and endonclease G (Endo G) pathway," Toxicology, Limerick, IR, vol. 218, No. 1, Jan. 20, 2006 (Jan. 20, 2006), pp. 1-12.

Chen, K.K., et al., The Alkaloids of Han-Fang-Chi, J. Biol. Chem., 1935, pp. 681-685, vol. 109.

Chen et al, "The Alkaloids of Han-Fang-Chi," J. Biol. Chern., 1935, pp. 681-685, vol. 109.

*Primary Examiner* — Kathrien A Cruz
(74) *Attorney, Agent, or Firm* — Mitchell Intellectual Property Law, PLLC

(57) ABSTRACT

Drug formulations, methods and their use in treatment of diseases using formulations of pure di-acid salts of tetrandrine family members, especially d-tetrandrine di-hydrochloride, combined with a pharmaceutical diluent or carrier.

4 Claims, No Drawings

TETRANDRINE FAMILY PHARMACEUTICAL FORMULATIONS AND METHOD

CROSS REFERENCE TO RELATED APPLICATIONS

The present application is a division of and claims the benefit of parent application Ser. No. 14/199,235, entitled TETRANDRINE FAMILY PHARMACEUTICAL FORMULATIONS AND METHOD, filed Mar. 6, 2014, which claims the benefit of U.S. Provisional Patent Application Ser. No. 61/792,849, entitled TETRANDRINE FAMILY PHARMACEUTICAL FORMULATIONS AND METHOD, filed on Mar. 15, 2013, the entire contents of which are incorporated by reference.

FIELD AND BACKGROUND OF THE INVENTION

The present invention relates to pharmaceutical formulations of a family of bisbenzylisoquinoline alkaloids. The specific family is referred to herein as the "tetrandrine family."

The tetrandrine family bisbenzylisoquinolines have two nitrogen locations and hence can exist in the free base form or as a mono or di-acid salt. Because of the enhanced solubility of the salt form of pharmaceutical ingredients, the salt forms are used in formulating pharmaceutical compositions. The active ingredient thus solubilizes more quickly and enters the bloodstream faster.

However, the di-acid chlorides of the tetrandrine family members, most importantly the dihydrochloride (DHC), are a difficult molecule to produce using standard pharmaceutical processing. As a result, all known formulators in the world use an in situ procedure as part of the compounding methodology. This leads to variations in content uniformity and tablet-to-tablet potency variances.

SUMMARY OF THE INVENTION

The present invention uses pure di-acid salts of tetrandrine family members, preferably d-tetrandrine, and most preferably d-tetrandrine di-hydrochloride, in pharmaceutical formulations. In a preferred embodiment, the di-acid salts are formed by spray drying. As used herein, the term "pure di-acid salt of a tetrandrine family member" means greater than 99% pure on an anhydrous basis.

DESCRIPTION OF THE PREFERRED EMBODIMENT

The tetrandrine family members have been found effective in treating multi-drug resistance in a variety of diseases and conditions, including cancer and malaria. See U.S. Pat. Nos. 5,025,020; 5,332,747; 6,528,519; 6,911,454; 6,124,315 and 6,962,927. The formulation of these active ingredients into suitable pharmaceutical delivery systems is thus very important.

The tetrandrine family members have the following structural formula:

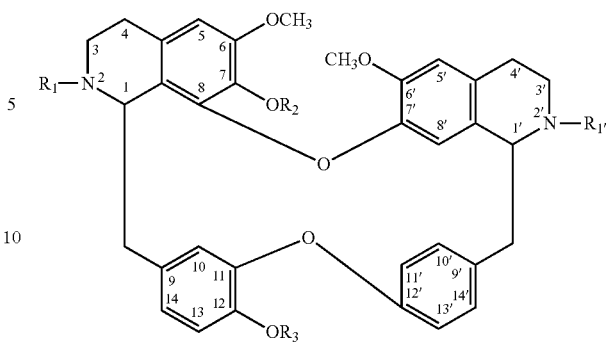

Where $R_1$ and $R_1'$ are the same or different shortchained carbon based ligand including without limitation, $CH_3$, $CO_2CH_3$ or H; and $R_2$ is $CH_3$ or $C_2H_5$; and $R_3$ is $CH_3$ or hydrogen; and where the chemical structure preferably has the "S" isomeric configuration at the C-1' chiral carbon location.

The preferred members of the tetrandrine family include the following representative examples, which are not intended to be exhaustive: d-tetrandrine, isotetrandrine, hernandezine, berbamine, pycnamine, phaeanthine, obamegine, ethyl fangchinoline and fangchinoline. In all of these examples, $R_1$ and $R_1'$ constitute the methyl group. Variation within the group occurs in that $R_2$ and $R_3$ may constitute either a methyl group or hydrogen, and the isometric configuration of the compounds at the C-1 and C-1' chiral carbon positions is either R (rectus) or S (sinister). The rules for R and S configuration can be found in Morrison and Boyd, "Organic Chemistry," $4^{th}$ Edition, copyright 1983 by Allyn and Bacon, at pp. 138-141. In addition, hernandezine includes a methoxy group at the C-5 position.

The most preferred member of the claimed tetrandrine family is d-tetrandrine. Methods for extracting and/or purifying d-tetrandrine are disclosed in U.S. Pat. No. 6,218,541 and in Published Patent Application No. 2011/0105755.

The di-acid salt of the tetrandrine family member is made by dissolving a purified member of the tetrandrine family, preferably d-tetrandrine, in exactly 2 molar equivalents of dilute acid, preferably hydrochloric acid (5-20% molar) in a vessel. The resulting clear solution is filtered to remove any residual solids into a glass feeding vessel. The solution is tested to assure that the potency of di-acid is within the specified limits. A spray drier is set with a wall temperature of 240-400 C. The atomizer is set to feed the di-acid salt solution at a rate of 1-2 liters/minute. The spray dried di-acid salt is captured in a poly bag lined container to yield 90-95% of the assayed di-acid salt in the feed solution. The solid di-acid salt is tested and released for formulation into capsules, though other dosage forms can be used. The di-acid salt used is preferably prepared from 99.9% pure tetrandrine family member, using exactly 2 equivalents of hydrochloric acid. The resulting solid di-acid salt contains only residual water and substantially no other impurities. As used herein, the term "pure di-acid salt of a tetrandrine family member" means greater than 99% pure on an anhydrous basis.

The dosage level used in humans will vary from case to case. However, it is anticipated that one would typically administer the tetrandrine family member drug at from about 50 to about 1000 mg per square meter per day, more preferably 250-700, and most preferably about 500, for from about 4 to about 14 days, during the course of treatment with a principle drug for treating the disease being treated.

The tetrandrine family members have known applications as primary or solo use drugs, as for example in the treatment of malaria, and in reducing hypertension. However, they are also known for use in conjunction with other drugs. The ratio of the tetrandrine family member to a principle or secondary drug will also vary from patient to patient, and from drug to drug, within a range of from about 0.04:1 to about 170:1. A more typical range would be from about 1:1 to 100:1, more preferably from 25:75 to 75:25.

The preferred formulations comprise a di-acid salt member of the d-tetrandrine family combined with a suitable pharmaceutical carrier. The pharmaceutical carrier can be a liquid or a solid composition. A liquid carrier will preferably comprise water, possibly with additional ingredients such as 0.25% carboxymethylcellulose. The solid carrier or diluent used is preferably pregelatinized starch. It may also be formulated with other ingredients, such as colloidal silicone dioxide, sodium lauryl sulfate and magnesium stearate. Exemplary Capsule Formulations Include the Following:

50 mg d-Tetrandrine di-hydrochloride
384 mg Pregelatinized Starch NF (Starch 1500)
4.4 mg Colloidal Silicon Dioxide (Cab-O-Sil M5)
0.4 mg Sodium Lauryl Sulfate NF
1.0 mg Magnesium Stearate NF;
100 mg d-Tetrandrine di-hydrochloride
70 mg microcrystalline cellulose
0.2 mg sodium lauryl sulfate
0.6 mg magnesium stearate; and
200 mg d-Tetrandrine di-hydrochloride
25.2 mg Pregelatinized Starch 1500 NF
1.5 mg Silicon Dioxide USP
0.25 mg Sodium Lauryl Sulfate NF
1.25 mg Magnesium Stearate USP.

Although the d-tetrandrine used in these formulations is the di-hydrochloride, the 50, 100 and 200 mg weights used the free base weights. Thus the actual amount of active used was slightly greater than the 50, 100 and 200 mgs indicated.

The 200 mg capsule formulation is most preferred. The most preferred dose of about 500 mg/square meter/day is roughly 1000 mg per day for a 190 pound patient six feet tall. Such a patient can fulfill the dosage requirements by taking five capsules during the course of the day, for example three in the morning and two in the evening, or one at a time spaced out over the day. A woman weighing 125 pounds at a height of five feet six inches would require four 200 mg capsules during the course of the day.

The various diseases which have been treated using tetrandrine family members in conjunction with principle drugs for treating the diseases, and the principle drugs used, are disclosed in U.S. Pat. Nos. 5,025,020; 5,332,747; 6,528,519; 6,911,454; 6,124,315 and 6,962,927.

Of course, it is understood that the forgoing are preferred embodiments of the invention, and that variations can be employed without departing from the spirit of the invention as set forth in the appended claims, interpreted in accordance with the principles of patent law.

The invention claimed is:

1. A method of forming the di-acid salt of a tetrandrine family member having the following formula:

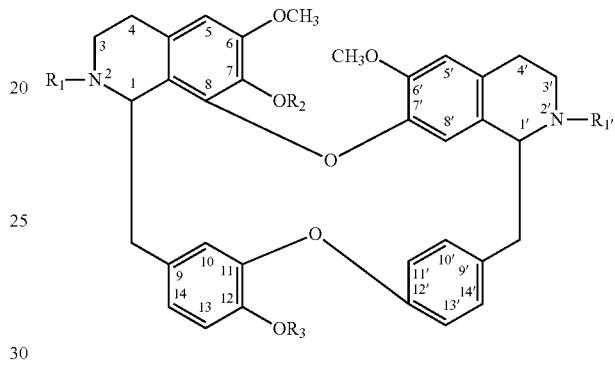

where $R_1$ and $R_1'$ are the same or different short chained carbon based ligand including without limitation, $CH_3$, $CO_2CH_3$ or H; and $R_2$ is $CH_3$ or $C_2H_5$; and $R_3$ is $CH_3$ or hydrogen, said method comprising: dissolving a purified member of the tetrandrine family in a 2 molar equivalent dilute acid solution, and feeding said solution through a spray drier.

2. The method of claim 1 in which said spray drier is set with a wall temperature of 240-400 C, and an atomizer set to feed the di-acid salt solution at a rate of 1-2 liters/minute.

3. The method of claim 2 in which said dilute acid solution is 5-20% molar hydrochloric acid.

4. The method of claim 3 in which said solution is filtered prior to spray drying to remove any residual solids.

* * * * *